United States Patent [19]

Szantay et al.

[11] 4,285,950
[45] Aug. 25, 1981

[54] 10-HALO-E-HOMOEBURNANE DERIVATIVES, A PROCESS FOR THE PREPARATION THEREOF, A PROCESS FOR THE USE THEREOF AS VASODILATORS, AND VASODILATING COMPOSITIONS THEREOF

[75] Inventors: Csaba Szántay; Lajos Szabó; György Kalaus; Lajos Dancsi; Tibor Keve; Ferenc Drexler, all of Budapest, Hungary

[73] Assignee: Richter Gedeon Vegyeszeti Gyar Rt, Budapest, Hungary

[21] Appl. No.: 175,383

[22] Filed: Aug. 5, 1980

[30] Foreign Application Priority Data

Aug. 13, 1979 [HU] Hungary ................................ RI 723

[51] Int. Cl.³ ................. C07D 471/22; A61K 31/395
[52] U.S. Cl. ............................. 424/256; 260/239.3 P; 260/245.7; 546/70
[58] Field of Search ...................... 260/239.3 P, 245.7; 424/256

[56] References Cited

U.S. PATENT DOCUMENTS

3,770,724  11/1973  Warnant et al. .............. 260/239.3 P

FOREIGN PATENT DOCUMENTS

2010833  7/1979  United Kingdom .............. 260/239.3 P

*Primary Examiner*—Robert T. Bond
*Attorney, Agent, or Firm*—Karl F. Ross

[57] ABSTRACT

The invention relates to new 10-halo-E-homoeburnane derivatives of the general formula (I), wherein $R^2$ is a $C_{1-6}$ alkyl group and X is halogen, and epimers, optically active derivatives and pharmaceutically acceptable acid addition salts thereof. These substances exert vasodilating effects and can be applied to advantage in the therapy.

The new compounds are prepared so that a racemic or optically active 9-halo-octahydroindoloquinolisine derivative of the general formula (II), wherein $R^2$ and X are as defined above and $R^1$ is a $C_{1-6}$ alkyl group, or an acid addition salt thereof is treated with a strong base, and, if desired, the 15-epimers of the resulting compound having the general formula (I) are separated from each other, and/or, if desired, the resulting substance is converted into its pharmaceutically acceptable acid addition salt and/or resolved.

7 Claims, No Drawings

10-HALO-E-HOMOEBURNANE DERIVATIVES, A PROCESS FOR THE PREPARATION THEREOF, A PROCESS FOR THE USE THEREOF AS VASODILATORS, AND VASODILATING COMPOSITIONS THEREOF

The invention relates to new 10-halo-E-homoeburnane derivatives of the formula (I),

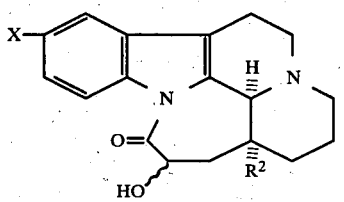

wherein $R^2$ is a $C_{1-6}$ alkyl group and X is a halogen, and pharmaceutically acceptable acid addition salts, epimers and optically active derivatives thereof.

The invention also relates to pharmaceutical compositions which contain at least one of the new compounds defined above, and to a process for the preparation of the new compounds and the pharmaceutical compositions.

The new compounds defined above are prepared according to the invention in that a racemic or optically active 9-halo-octahydroindoloquinolizine derivative of the general formula (II),

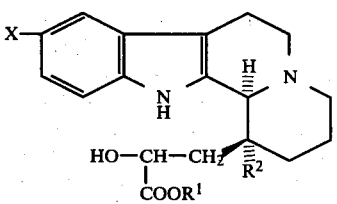

wherein $R^2$ and X are as defined above and $R^1$ is a $C_{1-6}$ alkyl group, or an acid addition salt thereof is treated with a strong base, and, if desired, the 15-epimers of the resulting compound having the formula (I) are separated from each other, and/or, if desired, the resulting substance is converted into its pharmaceutically acceptable acid addition salt and/or resolved.

The new compounds according to the invention possess valuable vasodilating effects, and they can also be utilized as intermediates in the preparation of other pharmaceutically active compounds, such as 10-halovincaminic acid esters.

In the compounds of the formulae (I) and (II) $R^1$ and $R^2$ can represent a straight-chain or branched $C_{1-6}$ alkyl group, such as methyl, ethyl, n-propyl, isopropyl, n-butyl, sec.-butyl, tert.-butyl, n-pentyl, isopentyl, n-hexyl or isohexyl group. $R^2$ represents preferably an ethyl or n-butyl group.

X may represent all the four halogens, i.e. fluorine, chlorine, bromine and iodine, preferably bromine.

The starting substances of the formula (II), where X, $R^1$ and $R^2$ are as defined above, can be prepared as follows; a 9-halo-1,2,3,4,6,7-hexahydroindolo[2,3-a]quinolizine derivative is reacted with a 2-acyloxyacrylic acid ester, and the resulting 1-(2'-acyloxy-2'-alkoxycarbonylethyl)-9-halo-1,2,3,4,6,7-hexahydroindolo[2,3-a]quinolizine derivative is first reduced and then deacylated, or first deacylated and then reduced.

Of the strong bases applicable in the process of the invention for converting the starting substances into the compounds of the formula (I), e.g. the following are to be mentioned: alkali metal hydrides, such as sodium hydride, alkali metal alcoholates, such as sodium methoxide, sodium ethoxide, sodium tert.-butoxide and potassium tert.-butoxide, alkali metal amides, such as sodium amide and potassium amide, alkali metal dialkylamides, such as lithium diisopropylamide.

This treatment can be performed in an inert aprotic non-polar organic solvent, such as an aromatic hydrocarbon (e.g. benzene, toluene or xylene). The starting substance is treated with the alkali preferably at or close to the boiling point of the solvent used.

The above reaction yields the compounds of the formula (I) as mixtures of 15-epimers. If desired, the individual epimers can be separated from each other preferably by preparative layer chromatography. When, however, the compounds of the formula (I) are to be converted later into 10-halovincaminic acid esters, the epimers need not be separated, since the subsequent reactions involve the elimination of the center of asymmetry in position 15.

It is preferred to use Merck $PF_{254+366}$ grade silica gel plates in the preparative layer chromatography. Various solvent combinations can be utilized as running and eluting agents.

The compounds of the formula (I) can be reacted with various acids to form the respective acid addition salts. Of the acids applicable in the salt formation step, e.g. the following are to be mentioned: mineral acids, such as hydrogen halides (e.g. hydrochloric acid or hydrogen bromide), sulfuric acid, phosphoric acid, nitric acid, perhaloic acids (such as perchloric acid), organic carboxylic acids, such as formic acid, acetic acid, propionic acid, glycolic acid, maleic acid, hydroxymaleic acid, fumaric acid, salicylic acid, lactic acid, cinnamic acid, benzoic acid, phenylacetic acid, p-aminosalicylic acid, p-aminobenzoic acid, p-hydroxybenzoic acid; alkylsulfonic acids, such as methanesulfonic acid; ethanesulfonic acid, cycloaliphatic sulfonic acids, such as cyclohexylsulfonic acid, arylsulfonic acids, such as p-toluenesulfonic acid, naphthylsulfonic acid, sulfanilic acid; amino acids, such as aspartic acid and glutamic acid.

If desired, the racemic compounds of the general formula (I) can be resolved in a manner known per se to obtain the respective optically active derivatives. The optically active end-products can also be prepared, however, from the appropriate optically active starting substances.

If desired, the racemic or optically active compounds of the formula (I) as well as the respective pure epimers and acid addition salts thereof can be subjected to further purification steps, such as recrystallization from an appropriately selected solvent or solvent mixture. The solvents or solvent mixtures utilized in this step are chosen in accordance with the solubility and crystallization characteristics of the substance to be purified.

The process of the invention yields the end-products in forms easy to identify. The analytical data, IR spectra, NMR spectra and mass spectra of the compounds prepared are in harmony with the assigned structures.

The compounds of the formula (I) were subjected to pharmacological tests in order to determine their effects on the circulation.

The tests were performed on dogs narcotized with chloralose urethane, and the arterial blood pressure, heart rate, and the blood flows in the arteria femoralis and arteria carotis interna were measured. Vascular resistances were calculated for the latter two vascular beds by the formula $$\text{vascular resistance} = \frac{\text{blood pressure}}{\text{blood flow}}$$

The substances under examination were administered as aqueous solutions in intravenous dosages of 1 mg/kg body weight. The tests were repeated five or six times. The results of the tests are listed in Table 1, whereas the corresponding properties of vincamine (reference substance) are given in Table 2.

The abbreviations used in the tables have the following meanings:
MABP: mean arterial blood pressure (mmHg)
HR: heart rate ($min^{-1}$)
CBF: blood flow in the carotis interna ($ml.min^{-1}$)
CVR: carotis vascular resistance ($mm\ Hg.min.ml^{-1}$)
FBF: femoral blood flow ($ml.min^{-1}$)
FVR: femoral vascular resistance ($mm\ Hg.min.ml^{-1}$)

TABLE 1

Circular effects of 10-bromo-14-oxo-15-hydroxy-E-homoeburnane-($3\alpha,17\alpha$) (mean values ± standard error)

|  | Control | Treated | Percentage difference |
|---|---|---|---|
| MABP | 146 ± 6.8 | 132 ± 9.8 | −9.6 |
| HR | 148 ± 16 | 139 ± 11 | −6.1 |
| CBF | 61.2 ± 13 | 74.0 ± 13 | +21 |
| CVR | 2.38 ± 0.52 | 1.78 ± 0.29 | −25 |
| FBF | 37.0 ± 7.8 | 37.2 ± 7.6 | +0.5 |
| FVR | 3.94 ± 0.61 | 3.55 ± 0.57 | −9.9 |

TABLE 2

Circular effects of vincamine (mean values ± standard error)

|  | Control | Treated | Percentage difference |
|---|---|---|---|
| MABP | 131 ± 5.2 | 112 ± 6.1 | −15 |
| HR | 181 ± 19 | 165 ± 15 | −9.1 |
| CBF | 39.2 ± 8.6 | 40.8 ± 8.5 | +4.1 |
| CVR | 3.35 ± 0.56 | 2.74 ± 0.52 | −18 |
| FBF | 35.9 ± 7.2 | 42.8 ± 7.4 | +19 |
| FVR | 3.65 ± 0.58 | 2.61 ± 0.53 | −28 |

The data indicate that 10-bromo-14-oxo-15-hydroxy-E-homoeburnane-($3\alpha,17\alpha$) hardly affects the blood pressure and the heart rate when administered to narcotized dogs in an intravenous dosage of 1 mg/kg body weight, i.e. it exerts favorably weak effects on the systemic circulation. The main effect of 10-bromo-14-oxo-15-hydroxy-E-homoeburnane-($3\alpha,17\alpha$) is the dilatation of arteria carotis, which may reach 25%, corresponding to a 21% increase in blood flow. It is particularly advantageous that this compound exerts practically no other effect on the circulation.

Because of their favorable vasodilating effects, the compounds according to the invention can be applied to advantage in therapy.

The new compounds according to the invention can be converted into pharmaceutical compositions for parenteral or enteral administration, utilizing conventional non-toxic, inert, solid or liquid pharmaceutical carriers, diluents and/or auxiliary agents. As carrier e.g. water, gelatine, lactose, starch, pectin, magnesium stearate, stearic acid, talc and vegetable oils such as peanut oil, olive oil, etc. can be applied. The pharmaceutical compositions can be presented in conventional forms, e.g. as solids (round or angular tablets, coated tablets, capsules, such as hard gelatine capsules, furthermore pills, suppositories, etc.) or liquids (such as oily or aqueous solutions, suspensions, emulsions syrups, soft gelatine capsules, injectable oily or aqueous solutions or suspensions, etc.). The amount of the solid carrier present may vary within wide limits; the solid compositions may contain preferably about 25 mg to 1 g of a carrier. If necessary, the pharmaceutical compositions may also contain conventional pharmaceutical additives, such as preservatives, wetting agents, emulsifying agents, salts for adjusting the osmotic pressure, buffers, flavoring agents, odorants, etc. If desired, the compositions may also contain other known pharmaceutically active substances in addition to the new compounds according to the invention. The pharmaceutical compositions are presented preferably in the form of unit dosages corresponding to the way of administration. The pharmaceutical compositions are prepared by methods well known in the pharmaceutical industry, such as sieving, mixing, granulating and pressing the components, dissolving the substances, etc. If desired, the compositions can also be subjected to other conventional pharmacotechnical operations, such as sterilization.

The invention is elucidated in detail by the aid of the following non-limiting Examples.

EXAMPLE 1

10-Bromo-14-oxo-15-hydroxy-E-homoeburnane-($3\alpha,17\alpha$)

0.30 g (2.7 mmoles) of potassium tert.-butoxide are added to a suspension of 3.0 g (6.9 mmoles) of 9-bromo-1$\alpha$-ethyl-1-(2-hydroxy-2-methoxycarbonyl-ethyl)-1,2,3,4,5,6,7,12-octahydro-12b$\alpha$H-indolo[2,3-a]quinolisine in 200 ml of dry toluene and 2.8 ml (2.6 g) of acetophenone, and the mixture is stirred and refluxed in an argon atmosphere for 4 hours. When the reaction terminates the mixture is cooled to 0° C. and shaken four times with 30 ml of cold 2.5% aqueous sulfuric acid, each. The aqueous acidic phases are combined, cooled, the pH of the solution is adjusted to 10 with 25% aqueous ammonia, and then extracted three times with 30 ml of dichloromethane, each. The organic phases are combined, dried over magnesium sulfate, filtered, and the filtrate is evaporated in vacuo. The residue is crystallized from 10 ml of methanol to obtain 1.85 g (66.6%) of the named compound as a mixture of epimers; m.p.: 206–208° C. The empirical formula of the product is $C_{20}H_{23}BrN_2O_2$ (mol.wt.:403.33).

The epimers are separated from the epimeric mixture by preparative thin layer chromatography. Kieselgel PF$_{254+366}$ grade silica gel plates, 20×20 cm in area and 1.5 mm in thickness, are applied as adsorbent, and a 14:3 mixture of benzene and methanol is utilized as solvent. The product is eluted with dichloromethane. The fast-moving epimer is termed as epimer "A", and the slow-moving epimer is termed as epimer "B". Epimer "A" is crystallized from 5 ml of methanol, and epimer "B" is crystallized from 10 ml of methanol.

0.4 g of epimer "A" are isolated from the upper spot, which corresponds to a yield of 21.6%. The substance melts at 177°–178° C.

IR spectrum (KBr): $\nu_{max.}$ 3400 $cm^{-1}$ (—OH), 1660 $cm^{-1}$ (amide—CO).

Mass spectrum (m/e): 404, 403, 402, 401, 376, 374, 360, 358, 347, 345, 332, 330, 317, 315, 303, 301, 277, 275, 180, 167, 153, 140.

1.25 g of epimer "B" are isolated from the lower spot; i.e. this epimer is obtained with a yield of 67.6%. The substance melts at 214–216° C.

IR spectrum (KBr): $\nu_{max}$. 3400 cm$^{-1}$ (—OH), 1685 cm$^{-1}$ (amide —CO).

Mass spectrum (m/e): 404, 403, 402, 401, 376, 374, 360, 358, 347, 345, 332, 330, 303, 301, 277, 275, 180, 167, 153, 140.

NMR spectrum (deuterochloroform): $\delta$ 0.96 (t, 3H,—CH$_3$), 7.39–8.24 (m, 3H, aromatic protons) ppm. $C_9$—H=7.51 ppm, $J_{12,9}$=0.2 Hz (para); $C_{11}$—H=7.39 ppm, $J_{11,12}$=8.7 Hz (ortho); $C_{12}$—H=8.24 ppm, $J_{11,9}$=2.8 Hz (meta).

What we claim is:

1. A compound of the formula (I),

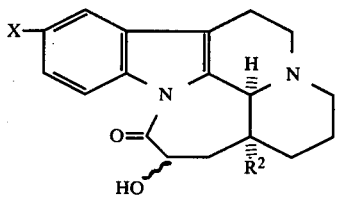

wherein R$^2$ is C$_{1-6}$ alkyl and X is halogen, or a pharmaceutically acceptable acid addition salt, an epimer or an optically active derivative thereof.

2. 10-Bromo-14-oxo-15-hydroxy-E-homoeburnane-(3α,17α).

3. A process for the preparation of a compound of the formula (I),

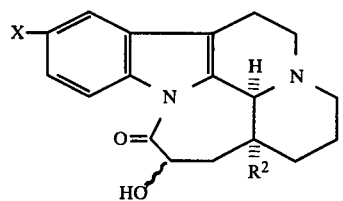

wherein R$^2$ is C$_{1-6}$ alkyl and X is halogen, or an epimer, an optically active component or a pharmaceutically acceptable acid addition salt thereof, wherein a racemic or optically active 9-halo-octahydroindoloquinolizine of the formula (II),

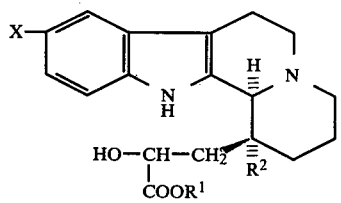

wherein R$^2$ and X are as defined above and R$^1$ is C$_{1-6}$ alkyl, or an acid addition salt thereof is treated with a strong base.

4. A process as claimed in claim 3, characterized in that an alkali metal alcoholate is used as the base.

5. A vasodilating composition which contains an amount of a compound as defined in claim 1 or an epimer, an optically active component or a pharmaceutically acceptable acid addition salt thereof, which is effective to produce vasodilation together with a conventional pharmaceutical carrier and/or diluent.

6. A vasodilating composition as claimed in claim 5, which contains as active ingredient 10-bromo-14-oxo-15-hydroxy-E-homoeburnane-(3α,17α).

7. A vasodilating method of treatment which comprises administering to an animal subject an amount of a compound as defined in claim 1 effective to produce vasodilation or an epimer, optically active component or a pharmaceutically acceptable acid addition salt thereof.

* * * * *